United States Patent
Rutledge et al.

(10) Patent No.: US 9,316,547 B1
(45) Date of Patent: Apr. 19, 2016

(54) METHOD FOR DETERMINING TIME-RESOLVED HEAT TRANSFER COEFFICIENT AND ADIABATIC EFFECTIVENESS WAVEFORMS WITH UNSTEADY FILM COOLING

(71) Applicant: The United States of America, as represented by the Secretary of the Air Force, Washington, DC (US)

(72) Inventors: James L. Rutledge, Fairborn, OH (US); Jonathan F. McCall, Colorado Springs, CO (US)

(73) Assignee: The United States of Americas represented by the Secretary of the AirForce, Washington, DC (US)

( * ) Notice: Subject to any disclaimer, the term of this patent is extended or adjusted under 35 U.S.C. 154(b) by 339 days.

(21) Appl. No.: 13/914,614

(22) Filed: Jun. 10, 2013

Related U.S. Application Data (60) Provisional application No. 61/657,700, filed on Jun. 8, 2012.

(51) Int. Cl.
*G01K 17/00* (2006.01)
*G01N 25/72* (2006.01)

(52) U.S. Cl.
CPC ............. *G01K 17/00* (2013.01); *G01N 25/72* (2013.01)

(58) Field of Classification Search
CPC combination set(s) only.
See application file for complete search history.

(56) References Cited

U.S. PATENT DOCUMENTS

| | | | |
|---|---|---|---|
| 4,963,499 A * | 10/1990 | Stockton | G01N 25/4846 165/263 |
| 7,040,805 B1 | 5/2006 | Ou et al. | |
| 2010/0129231 A1* | 5/2010 | Brittingham et al. | 416/97 R |

OTHER PUBLICATIONS

James L. Rutledge1 and Paul I. King2, "CFD Predictions of the Frequency Dependence of Pulsed Film Cooling Heat Flux on a Turbine Blade Leading Edge", 47th AIAA Aerospace Sciences Meeting Including The New Horizons Forum and Aerospace Exposition, Jan. 5-8, 2009.*

Ekkad, A Transient Infrared Thermography Method for Simultaneous Film Cooling Effectiveness and Heat Transfer Coefficient Measurement from a Single Test, Journal of Turbomachinery, Oct. 2004, vol. 126, pp. 597-603.

* cited by examiner

*Primary Examiner* — Lisa Caputo
*Assistant Examiner* — Nasir U Ahmed
(74) *Attorney, Agent, or Firm* — AFMCLO/JAZ; Jason Sopko (57) ABSTRACT

A new method for determining heat transfer coefficient (h) and adiabatic effectiveness (η) waveforms h(t) and η(t) from a single test uses a novel inverse heat transfer methodology to use surface temperature histories obtained using prior art approaches to approximate the h(t) and η(t) waveforms. The method best curve fits the data to a pair of truncated Fourier series.

5 Claims, 6 Drawing Sheets

METHOD FOR DETERMINING TIME-RESOLVED HEAT TRANSFER COEFFICIENT AND ADIABATIC EFFECTIVENESS WAVEFORMS WITH UNSTEADY FILM COOLING

CROSS REFERENCE TO RELATED PATENT APPLICATIONS

This application claims priority under 35 U.S.C. §119(e) from U.S. provisional application 61/657,700, filed Jun. 8, 2012, and titled "Method for Determining Time-Resolved Heat Transfer Coefficient and Adiabatic Effectiveness Waveforms with Unsteady Film Cooling." The invention description contained in that provisional application is incorporated by reference into this description.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to film cooling, and more specifically to a new method for determining heat transfer coefficient (h) and adiabatic effectiveness ($\eta$) waveforms h(t) and $\eta$(t) from a single test. The prior art has been able only to determine h and $\eta$ at moments in time, and not the waveforms, or equations, that allow better analysis, insight the ability to make predictions.

Traditional hot gas path film cooling characterization uses wind tunnel models to measure spatial adiabatic effectiveness ($\eta$) and heat transfer coefficient (h) distributions. By comparison with the heat transfer coefficient on a non-film-cooled model, a prediction of the net heat flux reduction due to film cooling can be formed. Periodic unsteadiness in the flow, however, causes fluctuations in both the adiabatic effectiveness and heat transfer coefficient. Generally, these fluctuations occur much faster than the thermal settling time of the model, making time resolved measurements of h and $\eta$ difficult, allowing a determination only of their average overall influence on the net heat flux reduction due to film cooling.

Film cooling protects hot gas path components by providing a layer of protective coolant between the surfaces and the hot freestream gas. The film effectively reduces the adiabatic wall temperature, $T_{aw}$, thereby reducing the driving potential for heat transfer. Film cooling also tends to affect the heat transfer coefficient, h, necessitating prediction or experimental measurement of $T_{aw}$ and h to accurately predict the heat flux into the surface. $T_{aw}$ is nondimensionalized in the form of the adiabatic effectiveness $\eta$, defined as:

$$\eta = \frac{T_\infty - T_{aw}}{T_\infty - T_c} \quad (1)$$

Eq. 1 facilitates prediction of $T_{aw}$ on a real engine component through measurement on a scaled experimental model at temperatures more convenient in a laboratory setting because $\eta$ is matched. The net heat flux reduction (NHFR) takes into account the effects on both $T_{aw}$ and h and quantifies the net benefit of film cooling in terms of heat load to a component with $T_s$ held at some acceptable temperature:

$$\Delta q_r \equiv 1 - \frac{q_f''}{q_0''} = 1 - \frac{h(T_{aw} - T_s)}{h_0(T_\infty - T_s)} \quad (2)$$

The h in Eq. (2) is often denoted $h_f$ to emphasize that it is measured with film cooling, but the subscript is not used in this description. The heat transfer coefficient without film cooling is represented by $h_0$. Some algebraic manipulation shows:

$$\Delta q_r = 1 - \frac{h}{h_0}\left(1 - \frac{\eta}{\phi}\right), \quad (3)$$

where $\phi$ is the nondimensionalized local surface temperature of the engine component, or overall effectiveness. Typically, $\phi$ is assumed to be in the vicinity of 0.6, but may be adjusted to correspond to a desired metal temperature.

If any unsteadiness is present that would cause fluctuations in $\eta$ or h, the NHFR is more meaningful in the time averaged sense. The time averaged NHFR may be written:

$$\overline{\Delta q_r} = 1 - \frac{\overline{h}}{h_0}\left(1 - \frac{\overline{\eta}}{\phi}\right) + \frac{\overline{h'\eta'}}{h_0\phi}, \quad (4)$$

with bars indicating time averaged quantities and the primes indicating zero-mean fluctuating components. Direct application of Eq. (4) requires time resolved measurements of h and $\eta$, which is difficult. The prior art developed a way around this problem by defining a new parameter that is easily measureable and takes into account the combined effects of the more difficult parameters to measure:

$$\gamma \equiv \overline{\eta} + \frac{\overline{h'\eta'}}{\overline{h}} \quad (5)$$

$\gamma$ is called the "unsteady coupled average adiabatic effectiveness." This parameter allows Eq. (4) to be rewritten as:

$$\overline{\Delta q_r} = 1 - \frac{\overline{h}}{h_0}\left(1 - \frac{\gamma}{\phi}\right) \quad (6)$$

The prior art teachings proved that $\gamma$ can be determined from the surface temperature on a film cooled model using infrared thermography and the following equation:

$$\gamma = \frac{T_\infty - \overline{T_s}}{T_\infty - T_c} - \frac{\overline{q_f''}}{\overline{h}(T_\infty - T_c)} - \frac{\overline{h'T_s'}}{\overline{h}(T_\infty - T_c)} \quad (7)$$

Direct application of Eq. (7) requires time resolved $T_s$ and h measurements as indicated by the last term on the RHS. This term may be kept negligible, however, provided that the heat capacity, $\rho c$, of the model material is sufficiently large that temperature fluctuations in the material are damped to negligible levels. To be precise, the nondimensional parameter that governs the temperature fluctuations is called C, defined as:

$$C = \sqrt{\frac{k\rho c\omega}{2\bar{h}^2}} \qquad (8)$$

The magnitude of $T_s'$ is inversely related to C. Such an experiment with large C yields $\gamma$ and $\bar{h}$, but not $\bar{\eta}$. Because this experimental technique requires only single temperature measurements for the $\gamma$ and $\bar{h}$ experiments, it naturally does not provide the time resolved waveforms of $\eta$ and h.

It is seen, therefore, that there is a need for being able to determine the h(t) and $\eta$(t) waveforms, and not just the values of h and $\eta$ at points in time.

SUMMARY OF THE INVENTION

The present invention is a novel inverse heat transfer methodology that can be used to approximate $\eta$(t) and h(t) waveforms. Unlike the prior art transient technique, this new methodology contains absolutely no assumption of steadiness in the formulation of the governing differential equations for heat transfer.

The technique is a modification of the prior art transient heat transfer technique that, with steady flow conditions only, allows the determination of $\eta$ and h from a single experiment by measuring the surface temperature history as the material changes temperature after sudden immersion in the flow. However, unlike the prior art transient technique, this new algorithm contains no assumption of steadiness in the formulation of the governing differential equations for heat transfer into a semi-infinite slab.

The method best curve fits the data to a pair of truncated Fourier series.

The technique was tested by devising arbitrary waveforms for $\eta$ and h at a point on a film cooled surface and running a computational simulation of an actual experimental model experiencing those flow conditions. The surface temperature history was corrupted with random noise to simulate actual surface temperature measurements and then fed into an algorithm developed here that successfully and consistently approximated the $\eta$(t) and h(t) waveforms.

The heat capacity, $\rho c$, of real materials suitable for laboratory testing has thwarted the ability of previous experimental methodologies of measuring the waveforms of periodic $\eta$ and h. At best, they could only determine the average effects of these two parameters. The present invention is the first to determine these important time-resolved parameters. The invention uses a novel inverse heat transfer methodology that does not rely on an analytical solution to the forward heat transfer problem with arbitrary $\eta$(t) and h(t) in the Robin boundary condition. This alleviates the previously insurmountable problem of the absence of a known solution to this differential equation. Furthermore, the invention does not require a step change in freestream temperature that previous methods that rely on Eq. 16 require. The freestream temperature must change during the experiment, but it may change in an arbitrary manner. Similarly, the coolant temperature need not remain constant over the duration of the experiment, but there is no requirement for it to change.

These and other features and advantages will become apparent in the following description.

BRIEF DESCRIPTION OF THE DRAWINGS

The teachings of the present invention will be better understood from the following drawings illustrating various aspects and example embodiments of the invention and its teachings.

DETAILED DESCRIPTION

The present invention provides an inverse heat transfer methodology to determine h(t) and $\eta$(t) waveforms. These waveforms can then be applied directly to Eq. (4) if desired, or examined to yield previously unattainable insight into the interactions between h and $\eta$. Additionally, the new methodology allows for determination of both waveforms with a single experiment.

Inverse Heat Transfer as Applied to Film Cooling

Traditional steady film cooling experiments are generally simple enough that they are rarely discussed in terms of inverse heat transfer. Before proceeding to the more complex case of unsteady $\eta$(t) and h(t), it is instructive to consider how inverse heat transfer techniques apply to prior art experiments.

A typical "forward" heat transfer problem is one in which a temperature distribution or heat flux (both may be a function of time) is sought from known boundary conditions. With the inverse problem, we normally have the temperature or heat flux data and wish to determine the boundary conditions. This is precisely the case with traditional film cooling experiments.

For example, consider a steady wind tunnel experiment from which we wish to determine $\eta$. The heat flux into the model may be written:

$$q = h(T_{aw} - T_s) \qquad (9)$$

$$T_{aw} = \frac{q}{h} + T_s \qquad (10)$$

or

Nondimensionalizing Eq. (10) using the definition of η:

$$\eta = \frac{T_\infty - T_s}{T_\infty - T_c} - \frac{q}{h(T_\infty - T_c)} \qquad (11)$$

The determination of η is often desired without prior knowledge of h or an accurate measurement of q. The experiment is thus typically conducted using a nearly adiabatic material so that the second term on the RHS of Eq. (11) is negligible, or at least small enough such that the error due to rough approximations for h and q cause little error in the measurement of η. (Note the similarity between Eqs. (11) and (7) when the last term on the RHS of Eq. (7) is kept small.) The methods used to account for the second term in Eq. (11) are varied. For example, it is common to cover the film cooling holes in the region of interest with tape to determine the influence of conduction by observing the surface temperature, which is different from $T_\infty$ even though the absence of film cooling dictates that η=0. In any event, this is a rudimentary use of inverse heat transfer methodologies—the boundary condition, Taw, is determined through a surface temperature measurement that differs slightly from $T_{aw}$.

Another popular prior art technique is more recognizable as an inverse heat transfer technique. In that methodology, a film cooled model is thermally soaked to a uniform and known temperature, $T_i$. The model is then suddenly exposed to flow conditions, resulting in a step change in boundary conditions. The transient surface temperature distribution is measured and the boundary conditions, $T_{aw}$ and h, are sought. Because the heat transfer is transient, Fourier's law of conduction must be applied to the problem. If the model and time length of the experiment is designed properly, one may assume that the conduction is locally one-dimensional and that the model behaves as a semi-infinite slab (the thermal wave never penetrates the material, i.e. $\sqrt{\alpha t_{max}}$<<thickness). In this case, conduction behaves according to the following differential equation with the indicated initial condition and boundary values:

$$k\frac{\partial^2 T}{\partial x^2} = \rho c \frac{\partial T}{\partial t} \qquad (12)$$

$$-k\frac{\partial T}{\partial x}\bigg|_{x=0} = h(T_{aw} - T_s(t)) \qquad (13)$$

$$T|_{t=0} T_i \qquad (14)$$

which implies:

$$T|_{x\to\infty} = T_i \qquad (15)$$

The convective heat flux boundary condition contains the unknown parameters (h and Taw) that are sought through knowledge of the resulting surface temperature as a function of time. Designing the experiment such that the model may be treated as a semi-infinite slab with a step change in boundary condition as above allows the use of a classic analytical solution to the above differential equation. The solution for the surface temperature response is available in heat transfer texts as:

$$\frac{T_s - T_i}{T_{aw} - T_i} = 1 - \exp\left(\frac{h^2 \alpha t}{k^2}\right) \operatorname{erfc}\left(\frac{h\sqrt{\alpha t}}{k}\right) \qquad (16)$$

In theory, only two surface temperature measurements need be recorded at different times after initiation of the experiment. Eq. (16) applies at both times and the two unknown parameters, h and $T_{aw}$, can be determined. More accuracy can be obtained through a least squares curve fit to many temperature measurements forming a time history of surface temperature.

As shown by its development, Eq. (16) is not applicable if there is any unsteadiness in either h or $T_{aw}$. In the present invention, an inverse heat transfer technique is developed not to simply determine two values, h and $T_{aw}$, but rather the functions h(t) and Taw(t). The boundary condition of Eq. (13) is replaced with:

$$-k\frac{\partial T}{\partial x}\bigg|_{x=0} = h(t)(T_{aw}(t) - T_s(t)) \qquad (17)$$

where h(t) and $T_{aw}$(t) are unknown periodic functions. No such classic analytical solution is known to exist for arbitrary waveforms of h(t) and $T_{aw}$(t). Texts present general solution methodologies for inverse heat transfer problems, but this problem is complicated by the absence of an analytical solution to the forward problem. This challenge necessitated the development of a new inverse heat transfer technique.

The Inverse Flux Solver for Arbitrary Waveforms (IFSAW)

The methodology according to the teachings of the present invention determine periodic h(t) and $T_{aw}$(t) waveforms from a surface temperature time history. The conduct of the experiment itself is quite similar to that described in the prior art; however, the data reduction algorithm differs markedly.

1. Cold soak an experimental model to a uniform and known temperature. A convenient temperature is the coolant temperature. This way, unsteady coolant can run through the cold soaked model prior to test initiation, reducing the number of events that must occur to begin the experiment.
2. Initiate the test by suddenly exposing the film cooled model to a freestream flow at a different, but known, temperature.
3. Measure the spatial surface temperature distribution as a function of time. The use of an infrared camera is a convenient way to do this, but the temperature data must be acquired fast enough to properly resolve the unsteady surface temperature response—this was not a criterion for the experimental equipment required for steady h and Taw. The calculations described herein are then performed at each individual pixel falling on the model surface. Alternatively, liquid crystals or discrete thermocouples could be used to provide surface temperature histories. Conclude the measurements before the thermal wave penetrates the thickness of the model material, i.e. $\sqrt{\alpha t_{max}}$<<thickness.
4. Seek the solution to the forward heat transfer problem for the surface heat flux. The surface temperature history is a Dirichlet boundary condition. The differential equation with associated boundary conditions is then:

$$k\frac{\partial^2 T}{\partial x^2} = \rho c \frac{\partial T}{\partial t} \tag{18}$$

$$T|_{x=0} = T_s(t) \tag{19}$$

$$T|_{t=0} = T_i \tag{20}$$

which implies:

$$T|_{x \to \infty} = T_i \tag{21}$$

Note that only the second boundary condition, Eq. (19), differs from the inverse problem with the boundary condition given by Eq. (13). The boundary conditions are known following the experiment, making this step a forward heat transfer problem. The first step in solving this forward problem is to filter the temperature data. Random noise in the data can have the effect of making the solution appear to have non-physical fluctuations in the heat flux. A third order Savitzky-Golay filtering is efficient and effective. Care must be taken in the application of the filter to ensure that the highest frequency fluctuations in η and h are not lost. The noise in the temperature data may very well limit this frequency. Two distinct approaches to solving the forward heat transfer problem have been used:

Computational Heat Transfer Simulation

In this approach, a simple time-marching one-dimensional second order accurate numerical heat transfer solver was written. The length of the computational domain should be selected such that it is an order of magnitude longer than $\sqrt{\alpha t_{max}}$ to ensure that indeed a semi-infinite slab is modeled. The temporal and spatial discretization should be selected such that the von Neumann stability requirement is satisfied:

$$\frac{\alpha \Delta t}{(\Delta x)^2} \leq \frac{1}{2} \tag{22}$$

At the surface, the temperature is simply set to the filtered experimental temperature data, which may be interpolated to provide sufficiently small Δt. Eq. (18) is solved within the domain using an adiabatic boundary condition, $$\frac{\partial T}{\partial x} = 0,$$

at the end of the domain. It is wise to ensure that the domain is long enough by recording the temperature at the end of the domain at the end of the simulation. This temperature should not differ significantly from the initial temperature. At each time step, the critical output is the surface heat flux, calculated from the surface temperature gradient.

$$q_s(t) = -k \frac{\partial T}{\partial x}\bigg|_{x=0} \tag{23}$$

Analytical Solution for Heat Flux

As an alternative to relying on a computational simulation to find the surface heat flux from the Dirichlet boundary condition, $T_s(t)$, an analytical solution exists for Eqs. (18) through (21). The prior art presents a solution $T(x,t)$ for an arbitrary surface boundary condition $T_s(t)$, after the semi-infinite slab is initially at a uniform temperature as:

$$T(x,t) - T_i = \frac{x}{2\sqrt{\pi \alpha}} \int_0^t f(\lambda) \frac{e^{-x^2/(4\alpha(t-\lambda))}}{(t-\lambda)^{3/2}} d\lambda \tag{24}$$

where $$f(t) = T_s - T_i \tag{25}$$

The temperature gradient is then found through differentiation and, ultimately, the surface heat flux may be written:

$$q_s(t) = \lim_{x \to 0} \frac{-2k}{x\sqrt{\pi}} \int_{x/(2\sqrt{\alpha t})}^{\infty} f\left(t - \frac{x^2}{4\alpha \mu^2}\right) e^{-\mu^2} (1 - 2\mu^2) d\mu \tag{26}$$

Because the function $f(t)$ is discrete, a numerical integration scheme must be employed.

Both methods described above to calculate $q_s(t)$ were confirmed to yield equivalent results through testing. The selection of either the analytical solution, which involves an improper integral, or the computational simulation is a choice to be made by the user and may be dependent on computational resources.

With $q_s(t)$ now in hand, the object is to find periodic $T_{aw}(t)$ and $h(t)$ functions that are least squares fits to:

$$q_s(t) = h(t)(T_{aw}(t) - T_s(t)) \tag{27}$$

Both $q_s(t)$ and $T_s(t)$ are now known. Truncated Fourier series may be used to approximate the periodic $T_{aw}(t)$ and $h(t)$ functions:

$$h(t) = \frac{\hat{h}_0}{2} + \sum_{n=1}^{N} \left(\hat{h}_n \cos\frac{n\pi t}{L} + \tilde{h}_n \sin\frac{n\pi t}{L}\right) \tag{28}$$

$$T_{aw}(t) = \frac{\hat{T}_0}{2} + \sum_{n=1}^{N} \left(\hat{T}_n \cos\frac{n\pi t}{L} + \tilde{T}_n \sin\frac{n\pi t}{L}\right) \tag{29}$$

In the above formulation, both waveforms are written with the same number of parameters, 2N+1, but there is no requirement to do so. Since it is likely that the same phenomenon that causes fluctuations in $T_{aw}$ also causes fluctuations in h, it is entirely reasonable to use the same number of terms to approximate each parameter. Also note that both waveforms written above use the same period length, L, for the same physical reasoning. Alternatively, different period lengths may be used in Eqs. (28) and (29); however, as will be explained below, the implementation of this inverse heat transfer methodology is facilitated somewhat by this valid assumption of common period length.

The object is to minimize ε, the sum of the square of the errors, across all NP data points by optimizing L and the vectors $\hat{h}_n$, $\tilde{h}_n$, $\hat{T}_n$, $\tilde{T}_n$ in:

$$\varepsilon = \sum_{i=1}^{NP} \left[ \begin{array}{l} q_s(t_i) - \left( \dfrac{\hat{h}_0}{2} + \sum_{n=1}^{N}\left( \hat{h}_n \cos\dfrac{n\pi t_i}{L} + \tilde{h}_n \sin\dfrac{n\pi t_i}{L}\right)\right) \times \\ \left(\left( \dfrac{\hat{T}_0}{2} + \sum_{n=1}^{N}\left( \hat{T}_n \cos\dfrac{n\pi t_i}{L} + \tilde{T}_n \sin\dfrac{n\pi t_i}{L}\right)\right) - T_s(t_i)\right) \end{array}\right] \quad (1)$$

Such an optimization procedure may be achieved through algorithms such as the Levenberg-Marquardt or trust-region methods. Good success has been experienced using the trust-region reflective algorithm implemented within Matlab. The choice of N, relating to the number of terms in the Fourier series depends on the fidelity with which one wishes to approximate the $T_{aw}(t)$ and h(t) waveforms. For the experimentation used in this description, used N=13 is used, thereby optimizing on a total of 55 parameters—2N+1 for each waveform and the period length, L. The optimization routine is quite insensitive to the initial guesses on the $\hat{h}_n$, $\tilde{h}_n$, $\hat{T}_n$ and $\tilde{T}_n$; however, a poor initial guess for L can result in failure to optimize. In many practical cases, the experimentalist may have a good idea of the lowest frequency expected in the waveforms. It may be the frequency of coolant pulsation or it may be the blade passing frequency. Nevertheless, the methodology of the present invention requires no such a priori knowledge.

The frequency content of the raw measured temperature data may be automatically determined through an appropriate application of a fast Fourier transform (FFT). Savitzky-Golay filtering may be used once again on the temperature data, but this time with a moving average spanning many cycles. This long-time moving average may be subtracted from the raw temperature data to observe the fluctuating component of the surface temperature. An FFT may then be performed on these temperature fluctuations to produce the single-sided amplitude spectrum. Of the multiple peaks expected to be seen, the lowest frequency peak is desired. A number of techniques exist to automatically locate this peak. One simple method is an algorithm to identify all local maxima that fall above 3 standard deviations above the mean of the amplitude spectrum. Of those identified peaks, select the one at the lowest frequency. Inverting this frequency provides a good initial guess to optimize on the period length, L. In any event, this is only a method to provide an initial guess to be refined during optimization; failure to optimize would indicate a poor initial guess, thereby removing the impact of subjectivity for this estimate.

If different period lengths, L, are used in Eqs. (28) and (29), then the described technique to acquire an initial guess would still only provide a single initial guess. A more robust optimization routine that is less sensitive to the initial guess on the period length might need to be used instead. Nevertheless, as stated earlier, the flow physics are probably such that the same phenomenon is responsible for fluctuations in both h and $T_{aw}$ so that L is the same for each.

Figure 1:
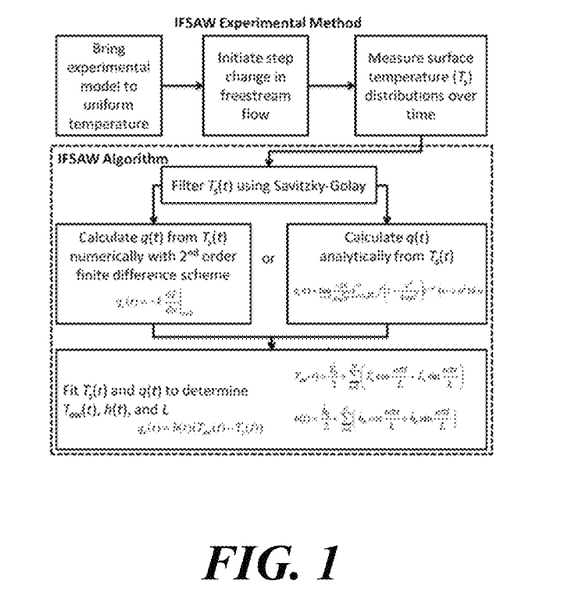
FIG. 1 is a flowchart showing a summary of steps for experiments and reducing data in accordance with the teachings of the present invention.

FIG. 1 is a flowchart showing a summary of steps for experiments and reducing data in accordance with the teachings of the present invention, referred to as the IFSAW algorithm.

Algorithm Testing Methodology

To test the IFSAW algorithm, it would be inappropriate to proceed immediately to a physical laboratory experiment. No other technique to reliably determine the both h and $T_{aw}$ waveforms is known to exist, so it would be difficult at this point to verify that the resulting waveforms are in fact, correct approximations for the true waveforms. As discussed in the prior art, the heat capacity, ρc, of the model can cause such dampening of the surface temperature fluctuations with periodic steady-state experiments that even determination of $\overline{\eta}$ is extremely difficult with that method, let alone the actual waveforms. Future experimental work with very slow fluctuations, however, may be able to test the algorithm.

Test Overview

Figure 2:
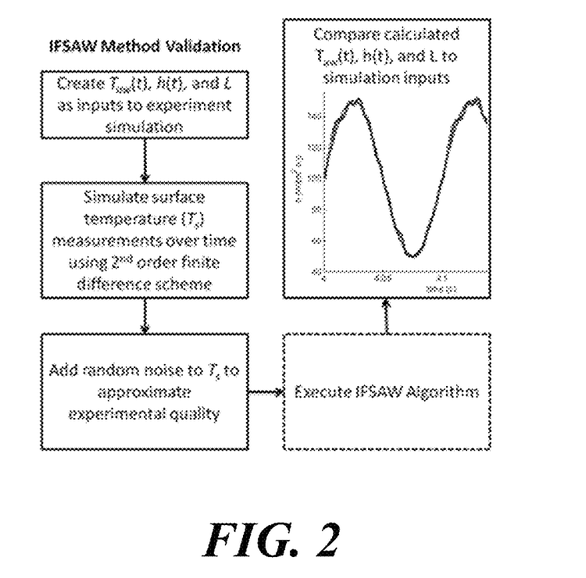
FIG. 2 is a flowchart of a validation procedure for the present invention.

For testing the algorithm, a computational simulation of the experiment was made. A variety of h and $T_{aw}$ waveforms were contrived, allowing the robustness of the IFSAW algorithm to be tested. A good data reduction algorithm must be able to handle not only the foreseen, but also the unexpected as the algorithm may be applied to handle unsteady heat transfer situations created by more than just simple coolant pulsing with a single frequency component. The contrived h and η waveforms were then input to a one-dimensional transient heat transfer simulator to determine the true surface temperature history following initiation of the transient experiment. The output of this simulation is termed "actual" data and would be impossible to physically measure—it represents the actual physical state of the test article under the prescribed conditions. Random error was then added to the temperature history to simulate laboratory measurements—this is the "measured" data. The noisy temperature history was then input to the IFSAW algorithm and the resulting waveforms compared to the originals. A summary of the validation procedure used in this study is provided in FIG. 2. Details regarding the implementation follow.

Test Details

A second order accurate finite differencing scheme was created to simulate the experiment. The code is similar to the IFSAW code that determines the surface heat flux from the Dirichlet boundary condition. This test simulator code, however, uses the Robin type surface boundary condition to determine the temperature profile through the slab. This surface boundary condition is given by Eq. (17), repeated here:

$$-k\left.\dfrac{\partial T}{\partial x}\right|_{x=0} = h(t)(T_{aw}(t) - T_s(t)) \quad (17)$$

For the experimental simulation we have prescribed h(t) and $T_{aw}(t)$ through the conversion:

$$T_{aw}(t) = T_\infty - \eta(t)(T_\infty - T_c) \quad (31)$$

$T_\infty$ and $T_c$ are selected according to what would be expected in the laboratory to simulate a situation in which η varies due to periodic unsteadiness in the coolant blowing rate. Alternative situations can be imagined in which $T_\infty$ and/or $T_c$ depend on time. The impact remains the same, though, in that $T_{aw}$ is a function of time. The time dependent values $T_\infty(t)$ and $T_c(t)$ would then be used in the nondimensionalization of $T_{aw}(t)$ to determine η(t). The initial condition of the simulation is the initial temperature of the model. As mentioned above, it is convenient from a practical standpoint to soak the model at the coolant temperature; $T_i = T_c$ was selected for the simulations.

Figure 3:
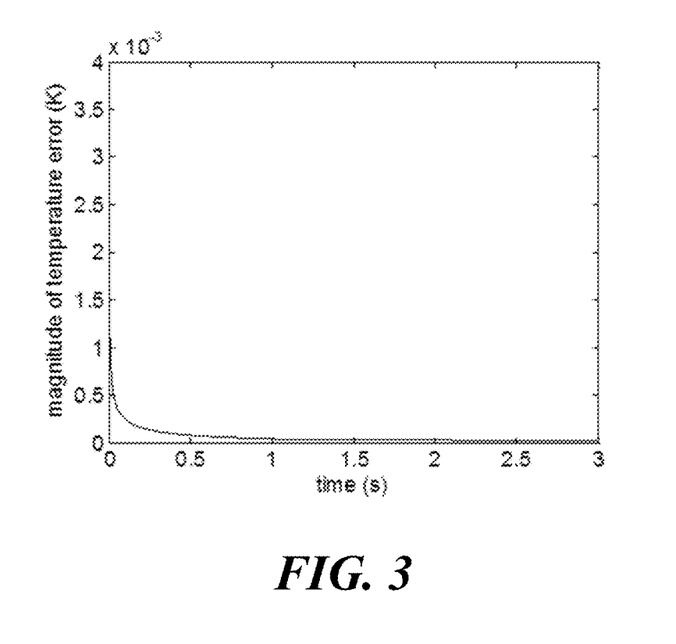
FIG. 3 is a graphical representation of the temperature error (K) in a numerical simulation of an experiment compared with an analytical solution for steady h and $\eta$.

It was critical to ensure that the transient simulation code functions properly. The code was validated using several techniques, including using steady h and η boundary conditions (Eq. (13)), for which a simple analytical solution for the surface temperature history exists (Eq. (16)). In this and all subsequent simulations, the model is assumed to be made of General Plastics Last-A-Foam FR-7106. The material properties and conditions for the simulation of the experiment are shown in Table 1. For the steady h and η validation case, η and h were simulated as η=0.4 and h=100 W/(m²K). The absolute value of the temperature error from the numerical simulation as compared with the analytical solution is plotted in FIG. 3. The largest error is at the beginning of the simulation when temperature gradients, both in time and space, are largest. Here, the error in temperature is a maximum of 0.0039 K at 0.5 ms after initiation.

TABLE 1

SIMULATED EXPERIMENTAL CONDITIONS AND MATERIAL PROPERTIES

| Property or Condition | Value | Source/Rationale |
|---|---|---|
| k | 0.03 W/(m K) | Property of Last-A-Foam FR-7106; From General Plastics |
| ρ | 96 kg/m³ | Property of Last-A-Foam FR-7106; From General Plastics |
| c | 1260 J/(kg K) | CRC Handbook |
| $T_c$ | 290 K | Easily achievable in lab with a chiller |
| $T_i$ | 290 K | same as $T_c$ - allows coolant to run through the cold soaked model prior to mainstream flow initiation |
| $T_\infty$ | 320 K | Easily achievable in lab with flow heater |
| $\epsilon_T$ | 0.1 K | temperature measurement uncertainty with 95% confidence |

Results

To demonstrate the IFSAW procedure with a practical example, the following simple waveforms for h and η were selected:

$$h = 100 + 50 \sin(2\pi \cdot 10t) \text{ W/(m}^2\text{K)} \quad (32)$$

$$\eta = 0.4 + 0.3 \sin(2\pi \cdot 10t) \quad (33)$$

These waveforms are in phase; that is, h is high when η is high as is usually the case. The parameters of 10 Hz and $\bar{h}$=100 W were selected as indicative of a 10× scale wind tunnel experiment roughly matching Reynolds number and nondimensional blade passing frequency order of magnitude with an actual engine. The selection of $\bar{\eta}$=0.4 is reasonable for a location downstream of a film cooling jet.

Figure 4:
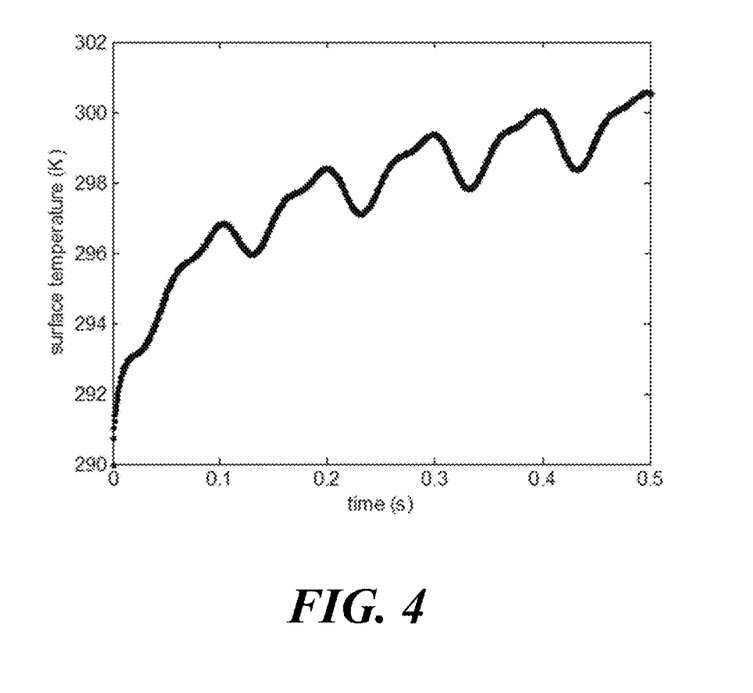
FIG. 4 is a graphical representation of surface temperature over the first 0.5 seconds of a simulated experiment with h=h=100+50 sin(2$\pi$·10t) and $\eta$=0.4+0.3 sin(2$\pi$·10t).

First, for the purposes of testing/demonstrating IFSAW, a numerical simulation of the experiment was ran using the parameters in Table 1. The first 0.5 seconds of the surface temperature response is shown in FIG. 4. Although the time step used in the numerical simulation was $10^{-5}$ seconds, temperature data was saved at 2 kHz, a more realistic laboratory data acquisition rate. Something about the choice of model materials for such an experiment can be immediately learned. During these first 0.5 seconds, the temperature rises from 290 K to just over 300 K. This is inconvenient for the experimentalist, who would prefer the temperature change at the beginning to be less rapid. This is often alleviated through the use of higher heat capacity materials such as acrylic instead of foam. Although fine for the steady film cooling experiments, higher heat capacity results in smaller surface temperature undulations, exacerbating the uncertainty in the ultimate goal of determining the h(t) and η(t) waveforms.

Figure 5:
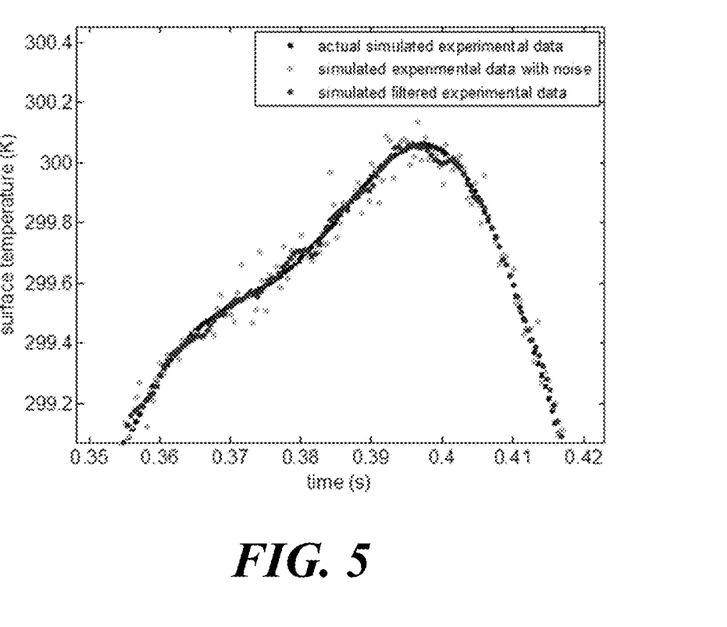
FIG. 5 shows a graphical representation of actual surface temperature, simulated noisy measured data with 0.1 K uncertainty and filtered data.

Temperature measurement noise is a major hurdle with inverse heat transfer and must be accounted for in simulations of experiments. In order to simulate real imperfect temperature measurements in the laboratory, a normally distributed random error with 95% confidence uncertainty of 0.1 K was added. This noisy data was then filtered using Savitzky-Golay filtering. The original "actual" temperature data along with the simulated "measured" noisy data and finally the filtered data are shown in FIG. 5 for a subset of the time period shown in FIG. 4. The filter is imperfect, but it cleans up the data well enough for use as the Dirichlet boundary condition to compute the surface heat flux.

Figure 6:
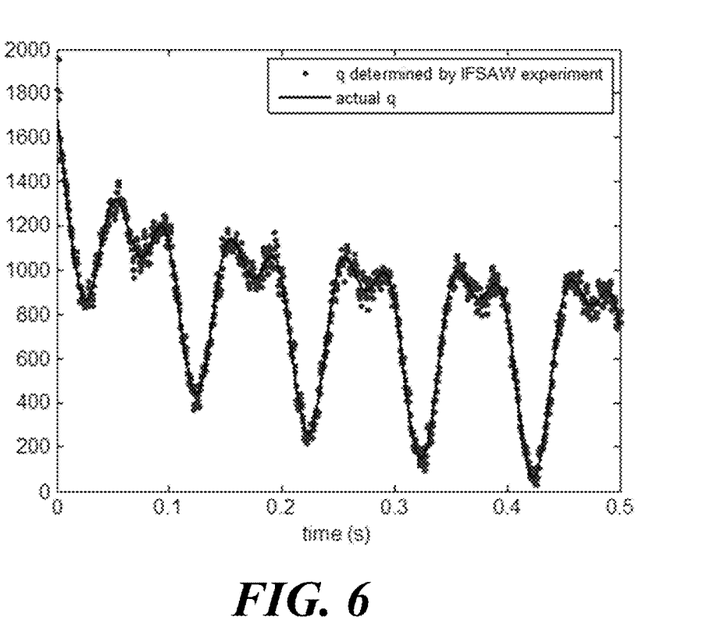
FIG. 6 shows a graphical representation of surface heat flux determined according to the teachings of the present invention compared to actual heat flux.

The heat flux was then calculated from the filtered surface temperature history and plotted in FIG. 6 along with the actual surface heat flux, provided as an output from the original simulation only for comparison purposes. The influence of measurement noise is apparent, but the least squares fits for the Fourier series approximations for h(t) and $T_{aw}(t)$ will be shown to be quite accurate, particularly by taking a longer set of data than the 0.5 seconds shown here.

Figure 7:
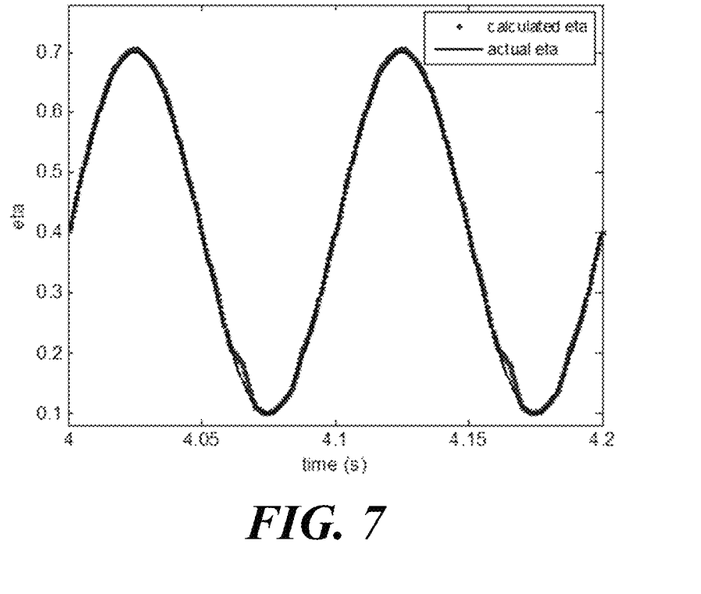
FIG. 7 is a graphical representation of an $\eta$(t) waveform determined with a 20 second simulated experiment with h=100+50 sin(2$\pi$·10t) and $\eta$=0.4+0.3 sin (2$\pi$·10t).
Figure 8:
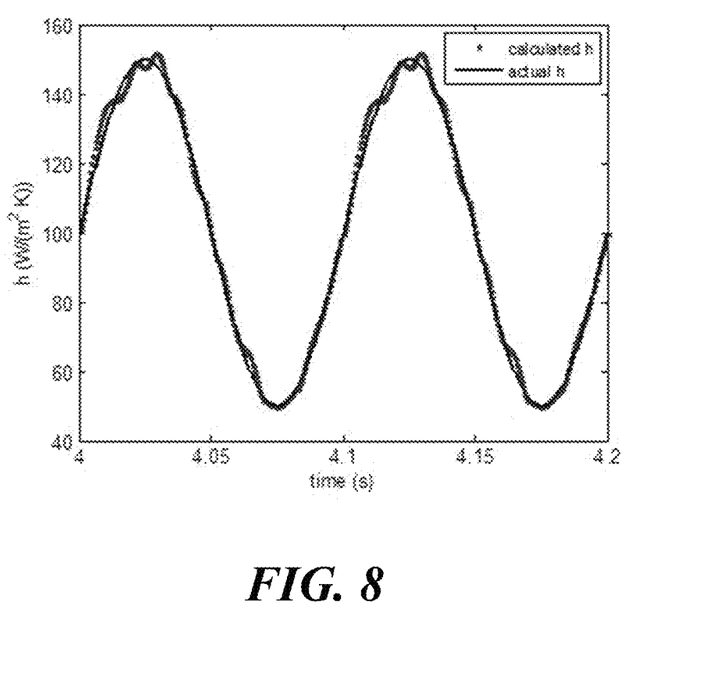
FIG. 8 is a graphical representation of an h(t) waveform determined with a 20 second simulated experiment with h=100+50 sin(2$\pi$·10t) and $\eta$=0.4+0.3 sin(2$\pi$·10t).

At this point, the number of terms to use in the Fourier series approximations (Eqs. (28) and (29)) must be chosen. For this simple contrived example, only a few terms are required (only 5 of the constants are non-zero); however, any a priori knowledge of the form of the result cannot be used to test the algorithm. Therefore, N=13 is used in Eqs. (28) and (29) for a total of 55 unknown constants to find through optimizing Eq. (30). Experimentation has found that this technique will provide decent approximations to even the more ill-behaved waveforms, as shown later. The simulation of the present example was run for 20 seconds of physical time and the waveforms output by the IFSAW algorithm are compared to the true waveforms in FIGS. 7 and 8. The influence of using "too many" terms in the Fourier series is evident; however, the approximations are decent. The approximations can then be used to calculate γ (through Eq. (5) and $\bar{h}$. These values are compared with the true values in Table 2.

Table 2 also gives the values that would be obtained if one erroneously assumed that h and η are constant and determined those values through a curve fit with Eq. (16). As it turns out, in this case, that curve fit happens to give decent values if we were to assume (again, erroneously) that γ=η as would be the case with steady film cooling (Eq. (5)). In any event, only the IFSAW data reduction technique yields the time resolved waveforms.

TABLE 2

| | γ | $\bar{h}$ (W/(m² K)) |
|---|---|---|
| Actual Values | 0.4750 | 100 |
| Values calculated from measurement | 0.4785 | 100.5831 |
| Legacy Technique that Assumes Constant h and η. | 0.4670 | 98.8744 |

The next set of tested waveforms contains several terms including a triangle wave to test the algorithm with a non-smooth function:

$$h = 100 + 10 \cdot \text{triangle}(2\pi \cdot 8t) + 30 \cdot \sin(2\pi \cdot 16t) \ldots + 10 \cdot \cos(2\pi \cdot 24t) + 5 \cdot \sin(2\pi \cdot 24t) + 5 \cdot \cos(2\pi \cdot 32t) \text{ W/(m}^2\text{K)} \quad (34)$$

$$\eta = 0.4 + 0.05 \cdot \text{triangle}(2\pi \cdot 8t) + 0.2 \cdot \sin(2\pi \cdot 8t) \ldots + 0.05 \cdot \sin(2\pi \cdot 40t) + 0.08 \cdot \cos(2\pi \cdot 32t) \quad (35)$$

Figure 9:
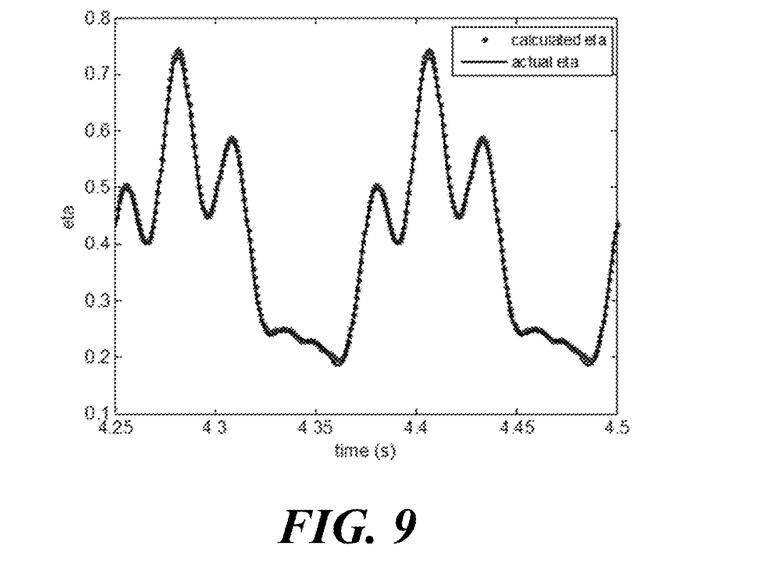
FIG. 9 is a graphical representation of an $\eta$(t) waveform determined with a 20 second simulated experiment with waveforms given by Eqs. (34) and (35).
Figure 10:
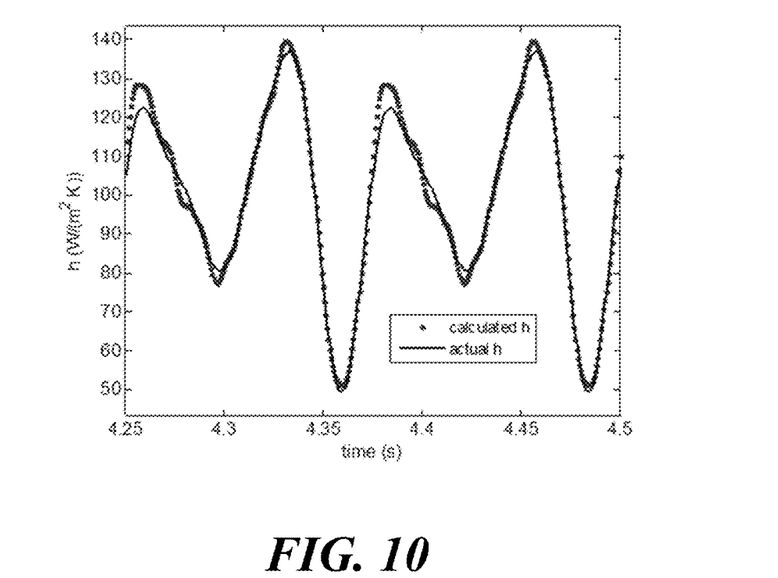
FIG. 10 is a graphical representation of an h(t) waveform determined by a 20 second simulated experiment with waveforms given by Eqs. (34) and (35).

Again, the simulated experiment was run for 20 seconds with random temperature uncertainty of 0.1 K. The algorithm properly determined the lowest frequency component to be 8 Hz and produced the results depicted in FIGS. 9 and 10. The actual value of γ for this condition is γ=0.4034 and the actual value of $\bar{h}$ is $\bar{h}$=100 W/(m²K). The values reported by analysis of the simulated measurements are γ=0.4068 and $\bar{h}$=100.69 W/(m²K).

Another 20 second experiment was simulated with the following waveforms:

$$h = 100 + 30 \cdot \text{triangle}(2\pi 8t) + 10 \cdot \sin(2\pi 16t) \ldots + 10 \cdot \cos(2\pi \cdot 24t) + 5 \cdot \sin(2\pi \cdot 24t) + 5 \cdot \cos(2\pi \cdot 32t) \text{ W/(m}^2\text{K)} \quad (36)$$

$$\eta = 0.4 + 0.2 \cdot \text{triangle}(2\pi \cdot 8t) + 0.04 \cdot \sin(2\pi \cdot 8t) \ldots + 0.05 \cdot \sin(2\pi \cdot 40t) + 0.08 \cdot \cos(2\pi \cdot 32t) + 0.01 \cdot \cos(2\pi \cdot 56t) \quad (37)$$

Figure 11:
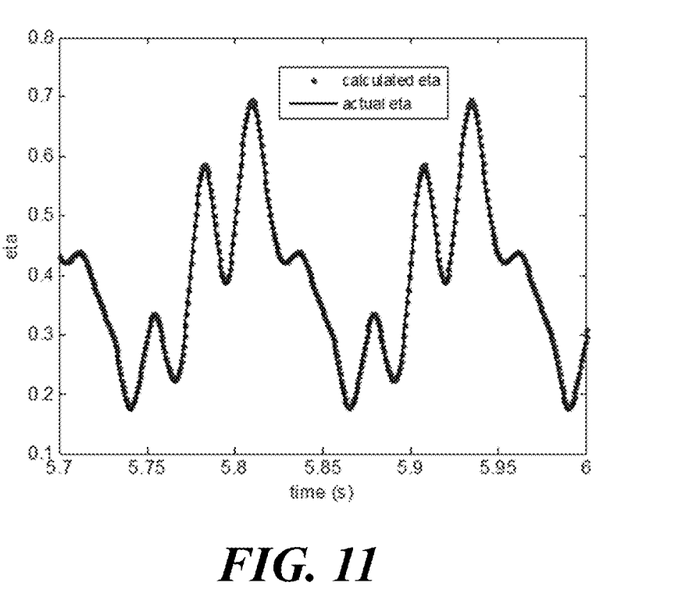
FIG. 11 is a graphical representation of an $\eta$(t) waveform determined with a 20 second simulated experiment with waveforms given by Eqs. (36) and (37).
Figure 12:
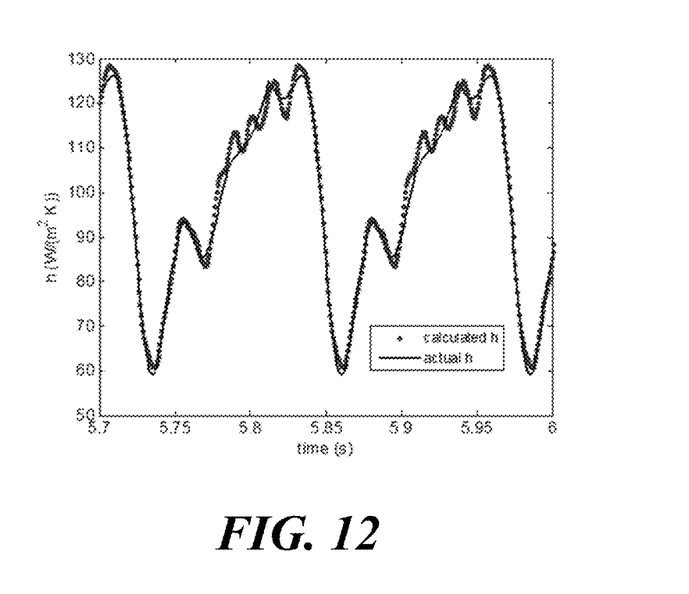
FIG. 12 is a graphical representation of an h(t) waveform determined with a 20 second simulated experiment with waveforms given by Eqs. (36) and (37).

FIGS. 11 and 12 depict those waveforms and the experimentally determined waveforms. The actual h(t) waveform contains a sharp discontinuity in its first derivative that manifests itself more harshly than in the case given by Eq. (34). The result is that the h(t) waveform is more difficult for the algorithm to approximate as seen in FIG. 12. The approximated waveform follows the true waveform well; however, it contains more unnatural oscillations.

Handling Imperfect Step Changes

In the preceding analysis, perfectly instantaneous placement of the film cooled model in the wind tunnel was presumed. In a real experiment, there would be some amount of time that is required for the freestream temperature to reach its steady state value; a true step change is impossible to achieve in a laboratory. Following how an experimentalist may account for this in data processing.

The model is assumed to be held initially at the coolant temperature and coolant flows through the model at an already-constant temperature. Freestream air at a higher temperature is turned on, but due to heat transfer taking place within the wind tunnel, the temperature ramps up to its final temperature over a finite period of time.

As discussed earlier, the invariance of η for a given set of flow conditions (identified through the Reynolds number and blowing ratio), irrespective of temperature, is a fundamental assumption in film cooling research. In other words, η is a function of the flow conditions, not an experiment's freestream and coolant temperatures. These temperatures are chosen for experimental reasons, such as measurement uncertainty or equipment limitations, but they do not change η. This invariance of η allows measurements made in the laboratory at temperatures cooler than engine temperatures to have practical application. Since η matches for the range of temperatures between a laboratory experiment and an actual engine, it certainly matches for small changes in $T_\infty$ that occur over the course of an experiment.

Assuming the velocity field immediately assumes its steady-state periodic condition after test initiation, the η(t) waveform must therefore also reach its steady-state periodic condition immediately, even though $T_{aw}$(t) does not due to thermal transients. In the special case of steady film cooling, this translates to a constant value of η, but a value of $T_{aw}$ that asymptotically approaches its final value. This assumption will not be completely accurate in a physical experiment because there is always a short amount of time during startup when the flowfield transitions to steady state. However, the aerodynamic transition to steady freestream flow should be, and in most cases is, very fast compared to the temperature transition.

In the discussion of the IFSAW algorithm earlier, a technique was described for finding a periodic function $T_{aw}$(t) that satisfies Eq. (27). For the more general case described here in which $T_\infty$ is allowed to ramp up over time, $T_{aw}$(t) is not a steady-state periodic function for the entire course of the experiment. Instead, the fact that η(t) is at a steady-state periodic condition throughout must be used. This is an implicit advantage of using IFSAW over Eq. (16) for any time-varying flow conditions: IFSAW does not require constant $T_{aw}$, but only a velocity field which reaches periodic steady state quickly.

To use IFSAW in this configuration, Eq. (1) is generalized to account for the sources of unsteadiness, including in $T_\infty$:

$$\eta(t) = \frac{T_\infty(t) - T_{aw}(t)}{T_\infty(t) - T_c} \quad (38)$$

Equation (27) can then be rewritten, eliminating $T_{aw}$:

$$\eta(t) = \frac{T_\infty(t) - T_{aw}(t)}{T_\infty(t) - T_c} \quad (39)$$

We now wish to find the periodic function for η(t) instead of $T_{aw}$(t), using a procedure otherwise identical to that described earlier. Just as high frequency $T_s$(t) measurements must be acquired, so too must $T_\infty$(t) measurements. Similarly a filtering technique (such as Savitzky-Golay) would be appropriate for the $T_\infty$(t) measurements to mitigate the effects of noise.

CONCLUSION

The described teachings of the present invention demonstrate a novel experimental technique and data reduction algorithm to determine η(t) and h(t) waveforms from a transient film cooling experiment. The conduct of the experiment itself is identical to one used in the prior art; however, the data acquisition rate must be high enough to resolve the unsteadiness that is of interest to the researcher. Traditional data processing techniques with transient film cooling experimental data yield only single values for η and h. This is perfectly acceptable only when the flow is steady. The solution to the conduction equation used in the traditional technique assumes a constant convective boundary condition; any departure from that represents a misapplication of that technique. The teachings of the present invention allow for periodic fluctuations in η and h. Not only does this new technique allow for proper determination of $\bar{h}$ and γ, but it also allows temporal resolution of approximate η(t) and h(t) waveforms.

Various other modifications to the invention as described may be made, as might occur to one with skill in the art of the invention, within the scope of the claims. Therefore, all contemplated example embodiments have not been shown in complete detail. Other embodiments may be developed without departing from the spirit of the invention or from the scope of the claims.

We claim:

1. A method for determining heat transfer coefficient h and adiabatic effectiveness η waveforms h(t) and η(t) from a single test on a film cooled test article, wherein η is determined from adiabatic wall temperature $T_{aw}$ as a dimensionless number $$\eta = \frac{T_\infty - T_{aw}}{T_\infty - T_c},$$

comprising the steps of:
(a) soak the test article to a uniform and known temperature;
(b) expose the test article to a freestream flow at a different and known temperature;
(c) measure spatial surface temperature $T_s$ as a function of time over a plurality of time steps, to determine $T_s(t)$;
(d) calculate surface heat flux $q_s(t)$ for each time step; and,
(e) find periodic $T_{aw}(t)$ and $h(t)$ functions that are least squares fits to:

$$q_s(t) = h(t)(T_{aw}(t) - T_s(t)),$$

using truncated Fourier series as the periodic $T_{aw}(t)$ and $h(t)$ functions; defined as:

$$h(t) = \frac{\hat{h}_0}{2} + \sum_{n=1}^{N} \left( \hat{h}_n \cos\frac{n\pi t}{L} + \tilde{h}_n \sin\frac{n\pi t}{L} \right); \text{ and,}$$

$$T_{aw}(t) = \frac{\hat{T}_0}{2} + \sum_{n=1}^{N} \left( \hat{T}_n \cos\frac{n\pi t}{L} + \tilde{T}_n \sin\frac{n\pi t}{L} \right).$$

2. The method for determining heat transfer coefficient and adiabatic effectiveness waveforms from a single test on a film cooled test article according to claim 1, wherein the step for finding least squares fit functions for $T_{aw}(t)$ and $h(t)$ comprises minimizing the sum of the square of errors across all data points $N_P$ by optimizing L and the vectors $\hat{h}_n, \tilde{h}_n, \hat{T}_n,$ and $\tilde{T}_n$, in:

$$\varepsilon = \sum_{i=1}^{N_P} \left[ \begin{array}{l} q_s(t_i) - \left( \frac{\hat{h}_0}{2} + \sum_{n=1}^{N} \left( \hat{h}_n \cos\frac{n\pi t_i}{L} + \tilde{h}_n \sin\frac{n\pi t_i}{L} \right) \right) \times \\ \left[ \left( \frac{\hat{T}_0}{2} + \sum_{n=1}^{N} \left( \hat{T}_n \cos\frac{n\pi t_i}{L} + \tilde{T}_n \sin\frac{n\pi t_i}{L} \right) \right) - T_s(t_i) \right] \end{array} \right]^2.$$

3. The method for determining heat transfer coefficient and adiabatic effectiveness waveforms from a single test on a film cooled test article according to claim 1, wherein the step for finding least square fit functions for $T_{aw}(t)$ and $h(t)$ includes selecting a starting period length L by inverting a frequency determined as the lowest frequency peak of the raw $T_s$, measurements over time using a fast Fourier transform (FFT).

4. A method for determining heat transfer coefficient h and adiabatic effectiveness $\eta$ waveforms $h(t)$ and $\eta(t)$ from a single test on a film cooled test article, wherein $\eta$ is determined from adiabatic wall temperature $T_{aw}$ as a dimensionless number $$\eta = \frac{T_\infty - T_{aw}}{T_\infty - T_c},$$

comprising the steps of:
(a) soak the test article to a uniform and known temperature;
(b) expose the test article to a freestream flow with a varying, but known temperature as a function of time;
(c) measure spatial surface temperature $T_s$ as a function of time over a plurality of time steps, to determine $T_s(t)$;
(d) calculate surface heat flux $q_s(t)$ for each time step; and,
(e) find periodic $\eta(t)$ and $h(t)$ functions that are least squares fits to:

$$q_s(t) = h(t)(T_\infty(t) - \eta(t)(T_\infty(t) - T_c(t)) - T_s(t)),$$

using truncated Fourier series as the periodic $\eta(t)$ and $h(t)$ functions; defined as:

$$h(t) = \frac{\hat{h}_0}{2} + \sum_{n=1}^{N} \left( \hat{h}_n \cos\frac{n\pi t}{L} + \tilde{h}_n \sin\frac{n\pi t}{L} \right); \text{ and,}$$

$$\eta(t) = \frac{\hat{\eta}_0}{2} + \sum_{n=1}^{N} \left( \hat{\eta}_n \cos\frac{n\pi t}{L} + \tilde{\eta}_n \sin\frac{n\pi t}{L} \right).$$

5. The method for determining heat transfer coefficient and adiabatic effectiveness waveforms from a single test on a film cooled test article according to claim 4, wherein the step for finding least squares fit functions for $\eta(t)$ and $h(t)$ comprises minimizing the sum of the square of errors across all data points $N_P$ by optimizing L and the vectors $\hat{h}_n, \tilde{h}_n, \hat{\eta}_n,$ and $\tilde{\eta}_n$ in:

$$\varepsilon = \sum_{i=1}^{N_P} \left[ \begin{array}{l} q_s(t_i) - \left( \frac{\hat{h}_0}{2} + \sum_{n=1}^{N} \left( \hat{h}_n \cos\frac{n\pi t_i}{L} + \tilde{h}_n \sin\frac{n\pi t_i}{L} \right) \right) \times \\ \left( T_\infty(t) - (T_\infty(t) - T_c(t)) \left( \frac{\hat{\eta}_0}{2} + \sum_{n=1}^{N} \left( \begin{array}{c} \hat{\eta}_n \cos\frac{n\pi t}{L} + \\ \tilde{\eta}_n \sin\frac{n\pi t}{L} \end{array} \right) \right) - T_s(t_i) \right) \end{array} \right]^2.$$

* * * * *